(12) United States Patent
Chin

(10) Patent No.: US 10,183,115 B2
(45) Date of Patent: Jan. 22, 2019

(54) SYRINGE FOR CORIUM REGENERATION

(71) Applicants: Joong Suk Jin, Seongnam-si (KR); Se Hoon Chin, Seongnam-si (KR)

(72) Inventor: Se Hoon Chin, Seongnam-si (KR)

(73) Assignees: Joong Suk Jin, Seongnam-si (KR); Se Hoon Chin, Seongnam-si (KR)

( * ) Notice: Subject to any disclaimer, the term of this patent is extended or adjusted under 35 U.S.C. 154(b) by 171 days.

(21) Appl. No.: 15/116,675

(22) PCT Filed: Feb. 2, 2015

(86) PCT No.: PCT/KR2015/001071
§ 371 (c)(1),
(2) Date: Aug. 4, 2016

(87) PCT Pub. No.: WO2015/119405
PCT Pub. Date: Aug. 13, 2015

(65) Prior Publication Data
US 2016/0346471 A1 Dec. 1, 2016

(30) Foreign Application Priority Data
Feb. 5, 2014 (KR) ........................ 10-2014-0013073

(51) Int. Cl.
*A61M 5/178* (2006.01)
*A61M 5/315* (2006.01)
(Continued)

(52) U.S. Cl.
CPC .......... *A61M 5/1782* (2013.01); *A61M 5/178* (2013.01); *A61M 5/31511* (2013.01);
(Continued)

(58) Field of Classification Search
CPC ............ A61M 2005/006; A61M 39/22; A61M 5/178; A61M 5/1782; A61M 5/31511; A61M 2005/3128; A61M 2005/31516
See application file for complete search history.

(56) References Cited

U.S. PATENT DOCUMENTS

| 4,838,866 | A | * | 6/1989 | Marshall, Sr. ......... A61D 1/025 |
| | | | | 417/443 |
| 5,484,421 | A | | 1/1996 | Smocer |
| | | | | (Continued) |

FOREIGN PATENT DOCUMENTS

| JP | 2004283714 | 10/2004 |
| JP | 2010525868 | 7/2010 |
| | (Continued) | |

OTHER PUBLICATIONS

International Search Report for International Application PCT/KR2015/001071, dated Apr. 17, 2015.

*Primary Examiner* — Brandy S Lee
(74) *Attorney, Agent, or Firm* — Burris Law, PLLC

(57) ABSTRACT

Disclosed is a syringe for corium regeneration. The syringe includes a cylinder formed as a thin tube having an inner diameter of 2-7 mm such that a liquid can be separated and stacked over a gas inside the cylinder; an inflow check valve provided on one side of the lower end of the cylinder such that a gas, which is supplied from the outside, can flow into the cylinder; and a needle coupled to the lower end of the cylinder, the upper end of the needle being positioned between a point which is 2 mm below the portion of connection of the inflow check valve and a point which is 5 mm above the portion of connection of the inflow check valve.

5 Claims, 5 Drawing Sheets

(51) Int. Cl.
*A61M 39/22* (2006.01)
*A61M 5/00* (2006.01)
*A61M 5/31* (2006.01)

(52) U.S. Cl.
CPC ....... *A61M 39/22* (2013.01); *A61M 2005/006* (2013.01); *A61M 2005/3128* (2013.01); *A61M 2005/31516* (2013.01)

(56) References Cited

U.S. PATENT DOCUMENTS

| | | |
|---|---|---|
| 2004/0182887 A1 | 9/2004 | Sugimura et al. |
| 2005/0074501 A1 | 4/2005 | Murphy et al. |
| 2012/0191036 A1* | 7/2012 | Chin .................... A61M 5/204 604/26 |

FOREIGN PATENT DOCUMENTS

| | | |
|---|---|---|
| KR | 1020110013796 | 2/2011 |
| KR | 1020120013271 | 2/2012 |
| WO | 2005032387 | 10/2005 |

* cited by examiner

[FIG. 1]
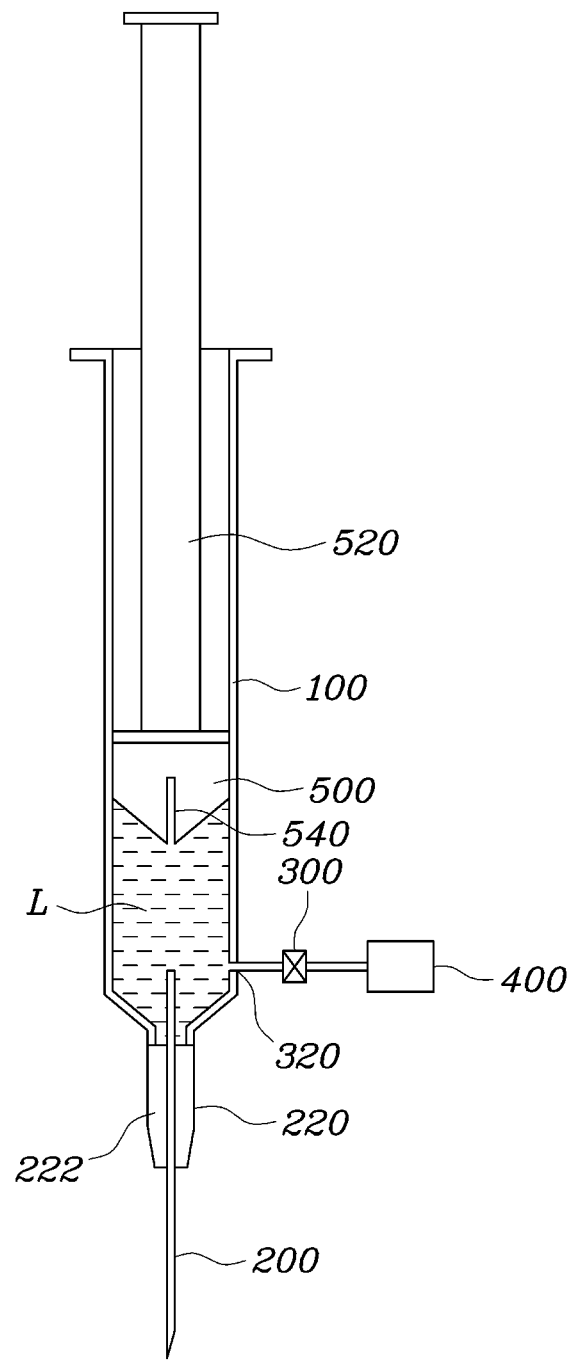

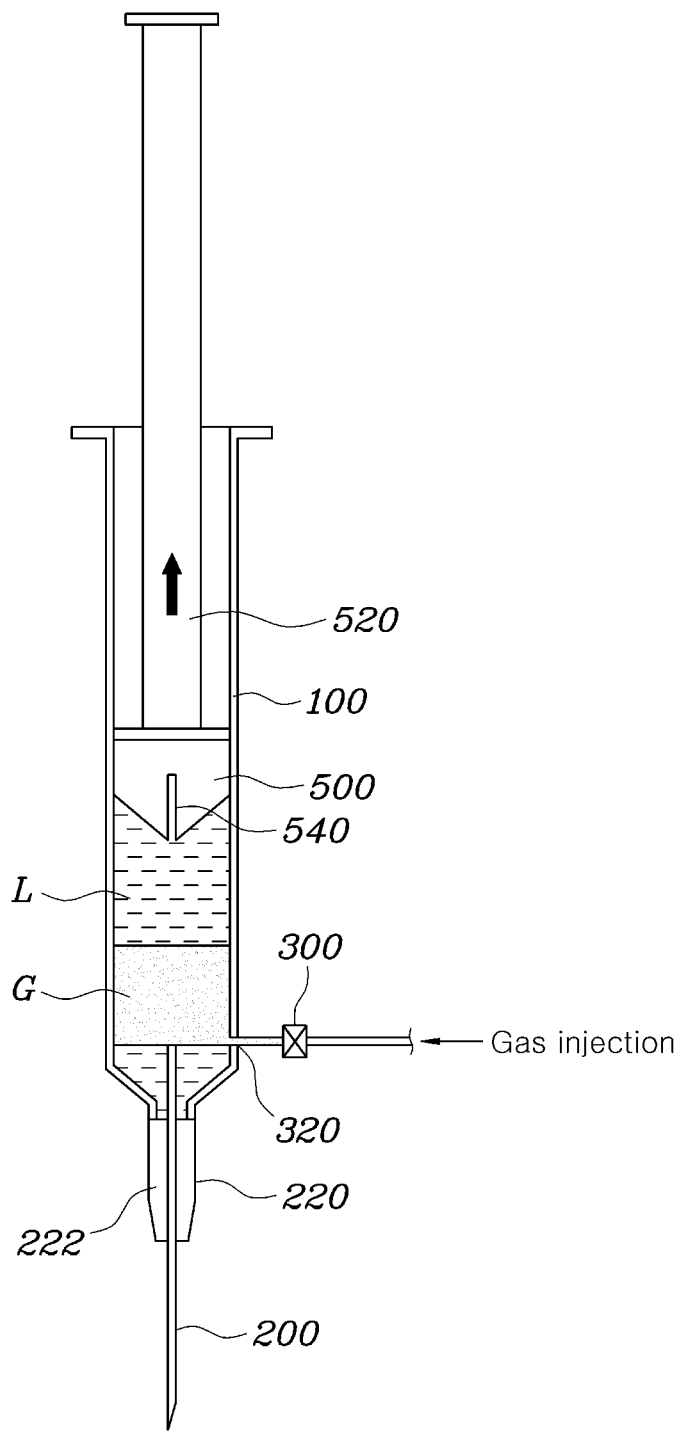
[FIG. 2]

[FIG. 3]
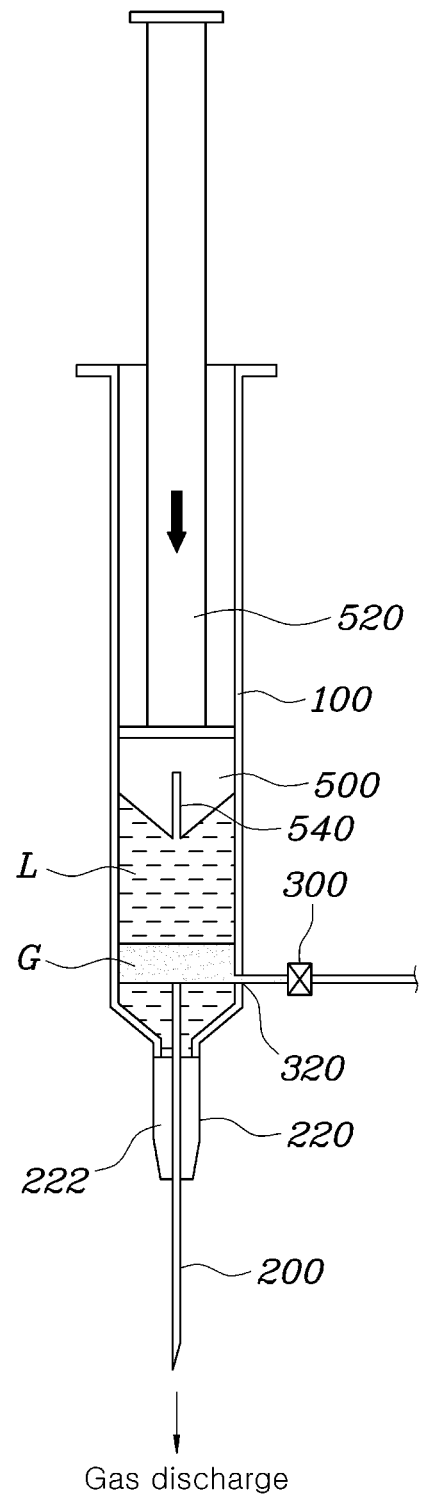
Gas discharge

[FIG. 4]
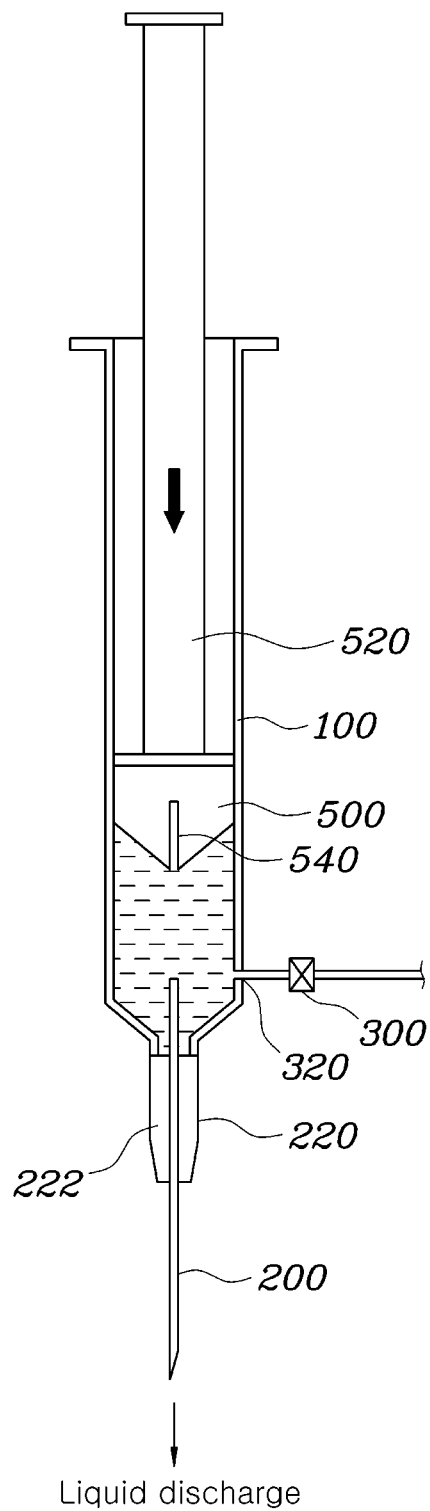
Liquid discharge

[FIG. 5]
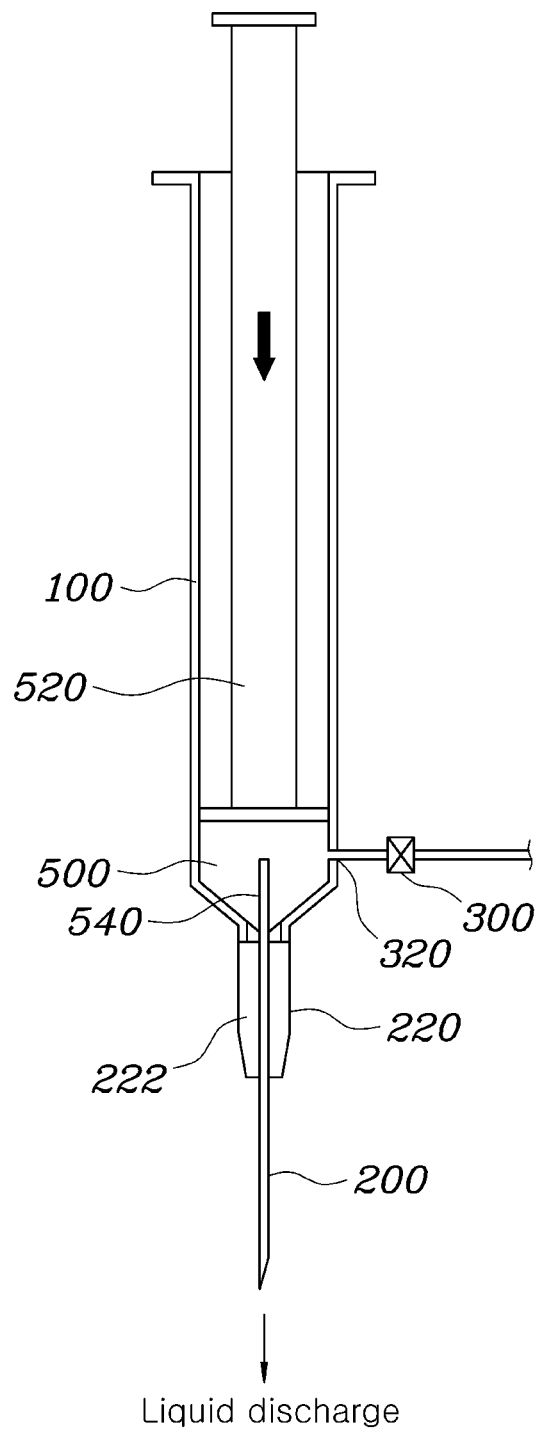

SYRINGE FOR CORIUM REGENERATION

CROSS-REFERENCE TO RELATED APPLICATIONS

This application is the United States national phase of International Application No. PCT/KR2015/001071 filed Feb. 2, 2015, and claims priority to Korean Patent Application No. 10-2014-0013073 filed Feb. 5, 2014, the disclosures of which are hereby incorporated in their entirety by reference.

TECHNICAL FIELD

The present invention relates to a syringe for corium regeneration that continuously and alternately injects gas and liquid into a corium layer of a skin by a desired amount.

BACKGROUND ART

In general, the corium is a part between an outer skin and a subcutaneous tissue of in the skin of the vertebrate animal, occurs from a mesoderm, and is a fiber connective tissue having a thickness of 0.3 to 2.4 mm. The corium includes sweat glands, hair follicles, fat lines and the like, and most of the physiological function of the skin occurs here.

A characteristic symptom of the skin aging is an occurrence of wrinkles in the skin. The wrinkles occur due to a situation in which the corium gets thinner and the elasticity is lost by the gradual regression of the extracellular matrix of the corium, thereby bending the outer skin over the corium. When medically explained, an amount of hyaluronic acid (HA) decreases on the corium layer with the aging of the skin, an elongation shape of fibroblast is collapsed due to a decrease in mechanical tension caused by fragmentation of a collagen lattice network. Thus, a decrease in production of collagen and regression progress and the corium is aged, with the result that the wrinkles occur in the upper skins.

In order to remove the wrinkles formed on the outer skin, an surgical operation for pulling and cutting the skin that has lost its elasticity, and an invasive method such as a chemical decortication for by making minutely damage to the outer skin to ensure that the skin is reproduced are also used. However, the invasive method has a disadvantage of having many side effects.

Meanwhile, there are non-invasive methods such as a Botox injection method for paralyzing the muscle for a certain period of time to prevent the occurrence of wrinkles, and a method for injecting a filler to the corium lower layer. In the case of Botox injection method, there is a disadvantage of a temporary effect (5 to 6 months). Although the Botox may prevent the wrinkles generated by the folded skin due to the movement of muscle by preventing the movement of the muscle, there are limitations that cannot solve the wrinkles that have already occurred even when the skin loses the elasticity and there is no contraction of muscle. Because it is practically impossible to correctly inject a uniform amount of filler into the corium layer just below the wrinkles, and an uneven irregular surface is made, it is hard to perform the method of injecting the filler into the corium layer. Further, because the filler is also absorbed after six to nine months, there is a disadvantage of a temporary effect.

Korean Patent Application No. 10-2012-0013271 A entitled "syringe for corium regeneration and treatment methods" is the applicant of the inventors of the present invention that discloses a syringe that injects a gas such as carbon dioxide into the corium layer of the wrinkled skin to apply a minute separation damage to the site of the corium layer, while the gas is widely diffused to the site, and injects a liquid such as hyaluronic acid or collagen solution diluted with water into the separation space formed accordingly.

When alternately injecting the gas and liquid into the corium layer or the corium lower layer of the skin in this way, the blood flow of the capillary of the corium layer increases, the active switching of the collagenous tissue is induced, new collagen is produced on the corium layer of the wide site, and the dense arrangement of fibers is formed. Thus, wrinkles of the upper outer skin are lost or get thinner. This method has no side effect, and has an advantage that the effect of the wrinkle removal is maintained for a long period of time.

Furthermore, as a result of the previous researches, it was checked that this treatment method has an excellent effect capable of easily curing the depression wounds of various forms such as laceration sink scar, chickenpox scar, pimple scar and nail mark which could not be solved by any existing surgical techniques such as fractional laser, decortication, chemical peeling and scar removal as well as wrinkle care.

However, in such a syringe, there was also a problem of a presence of a dead space in which liquid always remains at a location where a cylinder bottom and a syringe needle are coupled to each other. That is, because a check valve is provided in the cylinder of the syringe, liquid is always accumulated between the upper end of the needle and the check valve, and the gas cannot be introduced first.

Accordingly, even when the gas is injected into the syringe filed with liquid at the time of the initial production through the check valve, the liquid is always present in the dead space from the lower end of the check valve to the syringe needle. Accordingly, at the beginning of pushing of the piston after the invasion, there was a problem that some liquid is injected rather than the gas being injected into the corium, thereby failing to perform a perfect treatment effect.

Thus, there was an urgent need for injecting only the gas into the skin from the initial pressurization of the piston by suppressing dead space to a minimum.

Matters described as the background art are merely intended to facilitate the understanding of the background of the present invention, and should not be recognized as corresponding to the prior art that has been already known to those skilled in the art.

SUMMARY OF THE INVENTION

Technical Problem

An aspect of the present invention provides a syringe for corium regeneration that can allow only the gas to be injected into the skin from the initial pressurization of the piston by reducing the dead space between the lower end of the cylinder and the check valve to a minimum, and prevents the residual liquid or gas from remaining in the dead space even when repeatedly injecting the gas after the liquid injection or even when repeatedly injecting the liquid after the gas injection.

Technical Solution

According to an aspect of the present invention, there is provided a syringe for corium regeneration, the syringe including: a cylinder formed as a thin tube having an inner diameter of 2 to 7 mm such that a liquid can be separated and stacked over a gas inside the cylinder; an inflow check valve provided on one side of the lower end of the cylinder such that a gas supplied from the outside can flow into the cylinder; and a needle coupled to the lower end of the cylinder, an upper end of the needle being positioned between a point which is 2 mm below a connecting portion of the inflow check valve and a point which is 5 mm above the connecting portion of the inflow check valve.

A needle body is coupled to the lower end of the cylinder, the connecting portion of the inflow check valve is positioned above the needle body, the needle penetrating the needle body, and the upper end of the needle being positioned between the point which is 2 mm below the lower end of the connecting portion of the inflow check valve and the point which is 5 mm above the upper end of the connecting portion of the inflow check valve.

A blocking portion may be provided in the needle body to wrap around the needle and fill between the needle and an inner circumferential surface of the needle body.

The upper end of the needle may project upward through the blocking portion.

The syringe may further include a gas supply unit connected to the inflow check valve.

The syringe may further include a piston inserted into the cylinder.

An insertion groove into which the upper end of the needle is inserted may be formed at the lower end of the piston.

The lower end surface of the piston is in close contact with the lower end of the cylinder at a bottom dead center, and the upper end of the needle may be inserted into the insertion groove.

According to another aspect of the present invention, there is provided a syringe for corium regeneration, the syringe including: a cylinder formed as a thin tube having an inner diameter of 2 to 7 mm such that a liquid can be separated and stacked over a gas inside the cylinder; an inflow check valve provided on one side of the lower end of the cylinder such that a gas supplied from the outside can flow into the cylinder; and a needle flow passage coupled to the lower end of the cylinder, an upper end of the needle flow passage being positioned between a point which is 2 mm below a connecting portion of the inflow check valve and a point which is 5 mm above the connecting portion of the inflow check valve.

According to still another aspect of the present invention, there is provided a syringe for corium regeneration, the syringe including: a cylinder formed as a thin tube having an inner diameter of 2 to 7 mm such that a liquid can be separated and stacked over a gas inside the cylinder; an inflow check valve provided on one side of the lower end of the cylinder such that a gas supplied from the outside can flow into the cylinder; and a needle flow passage that is provided at the lower end of the cylinder an upper end of the need flow passage being formed to extend to a height upper corresponds to the connecting portion of the inflow check valve inside the cylinder.

Advantageous Effects

According to the syringe for corium regeneration having the aforementioned structure, it is possible to allow only the gas to be injected into the corium from the initial pressurization of the piston by suppressing the dead space between the lower end of the cylinder and the check valve to a minimum. Thus, it is possible to completely perform the repeated injection on the inside of the corium in the order of gas-liquid-gas.

Moreover, because all the liquid remaining in the cylinder can be used in the final step of finally using all the liquid, there is an advantage that is capable of using all the relatively expensive treatment liquid.

DESCRIPTION OF DRAWINGS

FIGS. 1 through 5 are diagrams illustrating an operation procedure of the syringe for corium regeneration according to the embodiment of the present invention.

DESCRIPTION OF THE INVENTION

Hereinafter, embodiments of the invention will be described in detail with reference to the accompanying drawings. The drawings are attached hereto to help explain exemplary embodiments of the invention, and the present invention is not limited to the drawings and embodiments. In the drawings, some elements may be exaggerated, reduced in size, or omitted for clarity or conciseness.

Hereinafter, a description will be given of a preferred embodiment of the present invention with reference to the accompanying drawings.

FIGS. 1 through 5 are diagrams illustrating an operation procedure of the syringe for corium regeneration according to the embodiment of the present invention. The syringe for corium regeneration according to the present invention includes a cylinder 100 formed as a thin tube having an inner diameter of 2 to 7 mm such that a liquid can be separated and stacked over a gas inside the cylinder; an inflow check valve 300 provided on one side of the lower end of the cylinder 100 such that a gas supplied from the outside can flow into the cylinder 100; and a needle 200 coupled to the lower end of the cylinder 100, an upper end of the needle being positioned between a point which is 2 mm below a connecting portion 320 of the inflow check valve 300 and a point which is 5 mm above the connecting portion 320 of the inflow check valve 300.

Like general syringes, the injector of the present invention includes a cylinder 100, a piston 500 positioned inside the cylinder, and a needle 200. However, since the cylinder 100 needs to use the surface tension and the viscosity of the liquid L filled therein, the cylinder 100 is formed as a thin tube having an inner diameter of 2 to 7 mm. The piston 500 includes a head and a support base 520.

Specifically, as shown in FIG. 1, a needle 200 is provided at a lower end of the cylinder 100 of the present invention. The needle 200 is inserted and coupled to the lower end of the cylinder 100 such that the upper end of the needle is positioned between a points which is 2 mm below the connecting portion 320 of the inflow check valve 300 and a point which is 5 mm above the connecting portion 320 of the inflow check valve 300.

The inflow check valve 300 is provided on one side of the lower end portion of the cylinder 100 such that the gas supplied from outside can flow into the cylinder 100. The check valve has characteristics of causing the fluid to pass only to one side such that the fluid does not pass to the outside from the inside of the cylinder 100, but the gas G can pass to the inside from the outside of the cylinder 100 through the inflow check valve 300. Thus, the gas G is filled into the cylinder 100 through the inflow check valve 300 and is discharged to the corium through the needle 200.

FIG. 1 shows a state in which the liquid L is initially filled in the cylinder 100. In the case of the liquid L, hyaluronic acid or collagen aqueous solution diluted with water is filled, and is injected into the space of the corium filled with the gas G. In this case, only the liquid for treatment is filled in the space formed between the lower end of the cylinder 100 and the piston 500 through a manufacturing process.

Thereafter, the gas G is filled in the interior of the cylinder 100 through the inflow check valve 300 as shown in FIG. 2. At this time, the external gas is supplied from the gas supply unit 400, and the gas supply unit 400 can maintain a constant pressure above an atmospheric pressure, such that the gas G can be filled in the interior of the cylinder 100 through the inflow check valve 300 as shown in FIG. 2, depending on the volume pulled when the user pulls the piston 500. Here, the upper end of the needle 200 is preferably provided to correspond to a point in which the connecting portion 320 of the inflow check the valve 300 is positioned. The reason is that, since there is a need to preferentially inject only the gas G rather than the liquid L into the corium at the start of the treatment, when limiting the upper end of the needle 200 in this manner, the gas G is filled from the upper end of the needle 200, and the gas G is preferentially discharged through the needle 200 at the initial pressurization of the piston 500 accordingly.

Further, because the inner diameter of the cylinder 100 is limited to 2 to 7 mm, even if the gas G is injected by the surface tension and the internal viscosity of the filled liquid L, the gas G pushes the liquid L, the liquid L is positioned on the top, the gas G is positioned at the bottom, and the upper end of the needle 200 is positioned immediately thereafter.

When the piston 500 is pressurized in this state as shown in FIG. 3, the gas G is first injected through the needle 200. After completing the injection of the gas G, some of the liquid L is injected, after invasive of the needle 200 to other parts of the skin, the gas G is filled again as shown in FIG. 2. Thereafter, processes of pushing the filled gas G into the corium as in FIG. 3 and injecting the liquid L again as shown in FIG. 4 are repeated to perform the treatment of corium regeneration.

That is, the processes of the gas G filling—the gas G injection—the liquid L injection—the gas G filling—the gas injection—the liquid L injection are repeatedly performed.

When the liquid L is substantially exhausted in the last step of such a treatment, as shown in FIG. 4, a process of finally injecting the liquid L is performed. Further, in this case, an insertion groove 540 into which the upper end of the needle 200 is inserted is formed at the lower end of the piston 500. When the piston 500 is fully pressurized and the piston 500 reaches the bottom dead center, as shown in FIG. 5, the bottom surface of the piston 500 is in close contact with the lower end of the cylinder 100, and the upper end of the needle 200 is inserted into the insertion groove 540, thereby injecting all of the remaining liquid L into the skin to finish the treatment.

Because the injected liquid L is hyaluronic acid or collagen aqueous solution diluted with water, the liquid is considerable expensive and some patients may feel burden. Thus, there is an advantage in which the treatment price becomes cheaper by using up all the liquid L.

Furthermore, it is possible to discharge all the liquid that remains below the upper end of the needle 200 when harmonizing the lower end of the piston 500 to match the lower end shape of the cylinder 100. At the same time, the needle body 220 is coupled to the lower end of the cylinder 100, and a blocking portion 222 can be provided in the needle body 220 to wrap around the needle 200 and fill between the needle 222 and the inner peripheral surface of the needle body 220. In this case, there is no dead space in the needle body 220 due to the blocking portion 222, and the liquid L is filled between the lower end of the cylinder 100 and the needle body 220 such that all of the residual liquid L can be discharged as shown in FIG. 5.

Meanwhile, the connecting portion 320 of the inflow check valve 300 is positioned above the needle body 220, the needle 200 penetrates the needle body 220, and the upper end of the needle can be positioned between a point which is 2 mm below the lower end of the connecting portion 320 of the inflow check valve 320 and a point which is 5 mm above the upper end of the connecting portion 320 of the inflow check valve 300. When the upper end is positioned at the bottom beyond 2 mm at the lower end of the connecting portion 320 of the inflow check valve 300, there is a problem in which the liquid rather than the gas is first injected by the dead space at the initial injection. When the upper end is positioned at the top beyond 5 mm from the upper end of the connecting portion 320 of the inflow check valve 300, there is a problem in which the residual gas excessively remains in the dead space between the upper end of the needle 200 and the connecting portion 320 of the inflow check valve 300. Thus, there is a problem in which the residual gas performs the role of a cushion due to the internal pressure of the residual gas after the gas is compressed above a certain level, and it is difficult to adjust the precise injection amount of liquid.

Thus, the upper portion of the needle 200 is preferably positioned between a point which is 2 mm below lower end of the connecting portion 320 of the inflow check valve 320 and a point which is 5 mm above the upper end of the connecting portion 320 of the inflow check valve 300. The upper end of the needle 200 which projects into the interior of the cylinder 100 is preferably fully inserted into the insertion groove 540 of the piston 500 such that only the gas G is discharged at the initial injection and all the liquid L fully discharged at the time of final injection.

A syringe for corium regeneration according to another aspect of the present invention includes a cylinder 100 formed as a thin tube having an inner diameter of 2 to 7 mm such that a liquid L can be separated and stacked over a gas G inside the cylinder; an inflow check valve 300 provided on one side of the lower end of the cylinder 100 such that the gas G supplied from the outside can flow into the cylinder 100; and a needle flow passage coupled to the lower end of the cylinder, an upper end of the needle flow passage being positioned between a point which is 2 mm below a connecting portion 320 of the inflow check valve 300 and a point which is 5 mm above the connecting portion 320 of the inflow check valve 300.

That is, the upper end of the needle 200 can extend upward on the inside of the cylinder 100 through a separate connecting tube extending upward, and in this case, the connecting tube can form a needle flow passage integrally with the needle 200 to substantially serve as the upper end of the needle 200.

According to the syringe for corium the regeneration having the aforementioned structure, it is possible to allow only the gas to be injected into the corium from the initial pressurization of the piston by suppressing the dead space between the lower end of the cylinder and the check valve to a minimum. Thus, it is possible to completely perform the repeated injection on the inside of the corium in the order of gas—liquid—gas.

Further, the upper end of the needle is positioned between a point which is 5 mm below the lower end of the inflow check valve and a point which is 2 mm above the upper end of the inflow check valve. Thus, it is possible to avoid a problem in the liquid discharge of precise amount, by preventing the ejection of the liquid at the time of the initial injection and restricting the residual gas to a minimum.

Moreover, because all the liquid remaining in the cylinder can be used in the final step of finally using all the liquid, there is an advantage that is capable of using all the relatively expensive treatment liquid.

While the present invention has been described and illustrated with reference to specific embodiments, it is obvious to those skilled in the art that the present invention can be variously improved and changed within the scope that does not depart from the technical idea of the present invention provided by the following claims.

The invention claimed is:

1. A syringe for corium regeneration comprising:
    a cylinder formed as a thin tube having an inner diameter of 2 to 7 mm such that a liquid can be separated and stacked over a gas inside the cylinder;
    a piston inserted into the cylinder;
    an inflow check valve provided on one side of a lower end of the cylinder such that a gas supplied from an outside of the syringe can flow into the cylinder;
    a needle body coupled to the lower end of the cylinder; and
    a needle coupled to the needle body,
    wherein the inflow check valve is connected to the cylinder at a connecting portion which is positioned above the needle body, and
    wherein the needle penetrates through the needle body, and an upper end of the needle is positioned between a point which is 2 mm below a lower end of the connecting portion of the inflow check valve and a point which is 5 mm above an upper end of the connecting portion of the inflow check valve; wherein an insertion groove, into which the upper end of the needle is inserted, is formed at a lower end of the piston.

2. The syringe for corium regeneration of claim 1, wherein a blocking portion is provided in the needle body to wrap around the needle and fill between the needle and an inner circumferential surface of the needle body.

3. The syringe for corium regeneration of claim 2, wherein the upper end of the needle projects upward through the blocking portion.

4. The syringe for corium regeneration of claim 1, further comprising: a gas supply unit connected to the inflow check valve.

5. The syringe for corium regeneration of claim 1, wherein a surface of the lower end of the piston is in close contact with the lower end of the cylinder at a bottom dead center, and the upper end of the needle is inserted into the insertion groove.

* * * * *